United States Patent [19]

Piepersberg et al.

[11] Patent Number: 5,656,453
[45] Date of Patent: Aug. 12, 1997

[54] PROCESS FOR THE PRODUCTION OF RECOMBINANT PROTEINS IN STREPTOMYCETES

[75] Inventors: Wolfgang Piepersberg, Wuppertal; Angela Weiss, Igersheim; Carola Rossler, Rodgau, all of Germany

[73] Assignee: Boehringer Mannheim GmbH, Mannheim, Germany

[21] Appl. No.: 313,168

[22] PCT Filed: Apr. 3, 1993

[86] PCT No.: PCT/EP93/00833

§ 371 Date: Mar. 31, 1995

§ 102(e) Date: Mar. 31, 1995

[87] PCT Pub. No.: WO93/20215

PCT Pub. Date: Oct. 14, 1993

[30] Foreign Application Priority Data

Apr. 7, 1992 [DE] Germany ............ 42 11 517.5

[51] Int. Cl.$^6$ ............ C12P 21/06; C12N 15/63; C12N 15/76
[52] U.S. Cl. ............ 435/69.1; 435/253.5; 435/320.1
[58] Field of Search ............ 435/69.1, 320.1, 435/253.5

[56] References Cited

U.S. PATENT DOCUMENTS 5,242,809  9/1993  Adams et al. ............ 435/69.1

OTHER PUBLICATIONS

Kämpfer et al., *J. Gen. Microbiol.*, 137:1831–1891 (1991).
Kieser et al., *Meth. Enzymol.*, 204:430–458 (1991).
Hütter et al., Actinomycetes in Biotechnology, *Academic Press*, London, 89–148 (1988).
Henderson et al., *J. Bacteriol.*, 169:3778–3784 (1987).
Hopwood et al., Genetic Manipulation of Streptomyces, A laboratory Manual, John Innes Foundation, Norwich (1985).
Chater et al., *Current Topics Microbiol.*, 46:69–95 (1982).
Bibb, M.J., Janssen, G.R., and Ward, J.M. 1985. Cloning and Analysis of the Promoter Region of the Erythromycin–Resistance Gene (ermE) of *Streptomyces erythraeus*. Gene, 38(1–3):215–226.

*Primary Examiner*—Douglas W. Robinson
*Assistant Examiner*—Thanda Wai
*Attorney, Agent, or Firm*—Felfe & Lynch

[57] ABSTRACT

The invention concerns a process for the production of recombinant proteins in streptomycetes in which the expression is carried out in *Streptomyces galbus* DSM 40480, preferably under the control of the ermE-up promoter or an inducible promoter.

5 Claims, 2 Drawing Sheets

PROCESS FOR THE PRODUCTION OF RECOMBINANT PROTEINS IN STREPTOMYCETES

The invention concerns a process for the production of recombinant proteins in streptomycetes in which the expression is carried out in *Streptomyces galbus* DSM 40480.

Streptomycetes are used on a large scale for the industrial production of various proteins. A review of 821 of these strains is given by P. Kämpfer et al. (J. of General Microbiology 137 (1991), 1831–1891).

Processes for the large-scale fermentation of streptomycetes have therefore been developed to an advanced stage and the use of streptomycetes in the production of therapeutic products has already been proven several times. Streptomycetes are also suitable for use in the recombinant production of proteins. The transformation processes necessary for this have already been described for many different streptomycetes strains (R. Hütter et al., in Actinomycetes in Biotechnology, eds. Goodfellow, Williams and Mordaski, Academic Press, London, 1988, 89–148; see in particular Table 10, p. 141–145). One problem with the expression of heterologous DNA in streptomycetes is, however, the cleavage of heterologous DNA, e.g. from *E. coli*, in genetically well characterized streptomycetes strains, such as for example *Streptomyces coelicolor*. The expression of heterologous proteins in *Streptomyces galbus* and *Streptomyces lividans* is described by A. Weiß et al. (6th German VAAM Workshop on the Biology of Streptomyces, Sept. 30–Oct. 3, 1990). *Streptomyces lividans* is preferred for the expression of heterologous proteins in streptomycetes since it shows a low cleavage activity towards heterologous DNA (T. Kieser et al. Meth. Enzymology 204 (1991), 430–458). The amount of protein which is obtained after expression in *Streptomyces lividans* is, however, unsatisfactory for large-scale production.

The object of the invention is therefore to provide a process for the production of recombinant proteins in streptomycetes in which the recombinant protein is obtained in a high yield.

This object is achieved by a process for the production of recombinant proteins in streptomycetes cells in which the cells are transformed with a vector that contains a DNA sequence coding for the protein, the transformed cells are multiplied such that the protein is expressed and the protein is isolated from the cells or the fermentation supernatant. This process is characterized in that the expression is carried out in *Streptomyces galbus* DSM 40480.

It surprisingly turned out that a substantially higher yield of recombinant protein is achieved when using *Streptomyces galbus* DSM 40480 than when using *Streptomyces lividans*. Thus serine protease B from *Streptomyces griseus* is obtained in a 10–50-fold higher yield after cloning and expression in *Streptomyces galbus* DSM 40480 than after cloning and expression in *Streptomyces lividans* under otherwise identical conditions (see FIG. 2).

Competent protoplasts of *Streptomyces galbus* DSM 40480 are preferably produced for the transformation by lysozyme treatment and freezing at −70° C. Transformation of these competent protoplasts with the vector DNA can be carried out in the presence of polyethylene glycol (PEG). After the transformation an incubation for 30 hours at 20°–25° C. is carried out in order to regenerate the protoplasts before selecting transformed streptomycetes. In order to express the heterologous DNA, the streptomycetes are then cultured in a suitable complex or synthetic medium. The selection of suitable media known to a person skilled in the art essentially depends on the heterologous protein to be produced and thus on the purification steps to be used. The recombinant protein is then isolated from the cells or from the fermentation supernatant according to known processes.

An expression vector is preferably used for the production of the recombinant protein in which the DNA sequence coding for the recombinant protein is under the control of a strong promoter. The ermE promoter (M. Bibb et al., Gene 41 (1986) 357–368) of the erythromycin resistance gene (ermE) from *Saccharopolyspora erythreus* is particularly preferred. The ermE promoter is understood to also include derivatives and alleles of this promoter which are obtained by deletion, substitution, insertion as well as by addition of nucleotides which cause initiation of transcription. Hybrid promoters which contain parts of the ermE promoter are also suitable. Use of a derivative of the ermE promoter which is denoted ermE-up promoter and the sequence of which is shown in SEQ ID NO: 1 is also preferred.

In addition it is preferred that the DNA sequence coding for the recombinant protein is under the control of an inducible promoter.

A suitable inducible promoter is, for example. The Gal P1 promoter from the galactose operon of *Streptomyces lividans* (Fornwald et al., Proc. Natl. Acad. Sci. USA 84 (1987), 2130–2134). A hybrid promoter, e.g. from the ermE-up promoter and the Gal P1 promoter, that enables an inducible high expression in streptomycetes can also preferably be used.

*Streptomyces galbus* strain DSM 40480, *E. Coli* HB 101 with pIJ699 (DSM 7031) and *E. coli* JM83 with pIJ4070 (DSM 7032) were deposited for the purpose of patent proceedings on 3rd Apr. 1992 at the "Deutsche Sammlung für Mikroorganismen und Zellkulturen GmbH, Mascheroder Weg 1b, 3300 Braunschweig".

The invention is elucidated in more detail by the following examples in conjunction with the Figures and the sequence protocols.

SEQ ID NO: 1 shows the sequence of the ermE-up promoter.

SEQ ID NO: 2 and
SEQ ID NO: 3 show the PCR primers used for the cloning and mutagenesis of the sprB signal peptide.

SEQ ID NO: 4 and
SEQ ID NO: 5 show the PCR primers used for cloning serine protease B from *Streptomyces griseus*.

SEQ ID NO: 6 and
SEQ ID NO: 7 show the PCR primers used for cloning alkaline phosphatase from *E. coli*.

SEQ ID NO: 8 and
SEQ ID NO: 9 show the PCR primers used for cloning human colipase.

SEQ ID NO: 10 and
SEQ ID NO: 11 show the PCR primers used for cloning human pancreatic amylase.

EXAMPLE 1

Construction of the Expression Vector pCRW69

The vector pIJ699 (T. Kieser et al., Gene 65 (1988), 83–91) is digested with the restriction endonucleases KpnI and BglII and the resulting 4.27 kb large fragment is ligated with a promoter-signal peptide multilinker cassette.

The sequence coding for the signal peptide is isolated from the gene sprB coding for the serine protease B of

*Streptomyces griseus* (DSM 40236) (the sequence of the sprB gene is given in: Henderson et al., J. Bacteriol 169 (1987), 3778–3784). It comprises the sequence coding for the signal peptide including the ribosome binding site and a section following the cleavage site of the signal peptidase in the gene product. This region is obtained by amplification with partially non-homologous primers (SEQ ID NO: 2 and 3) and altered in this process by a BamHI/SmaI restriction in such a way that it becomes accessible as a 150 bp long fragment.

Figure 1:
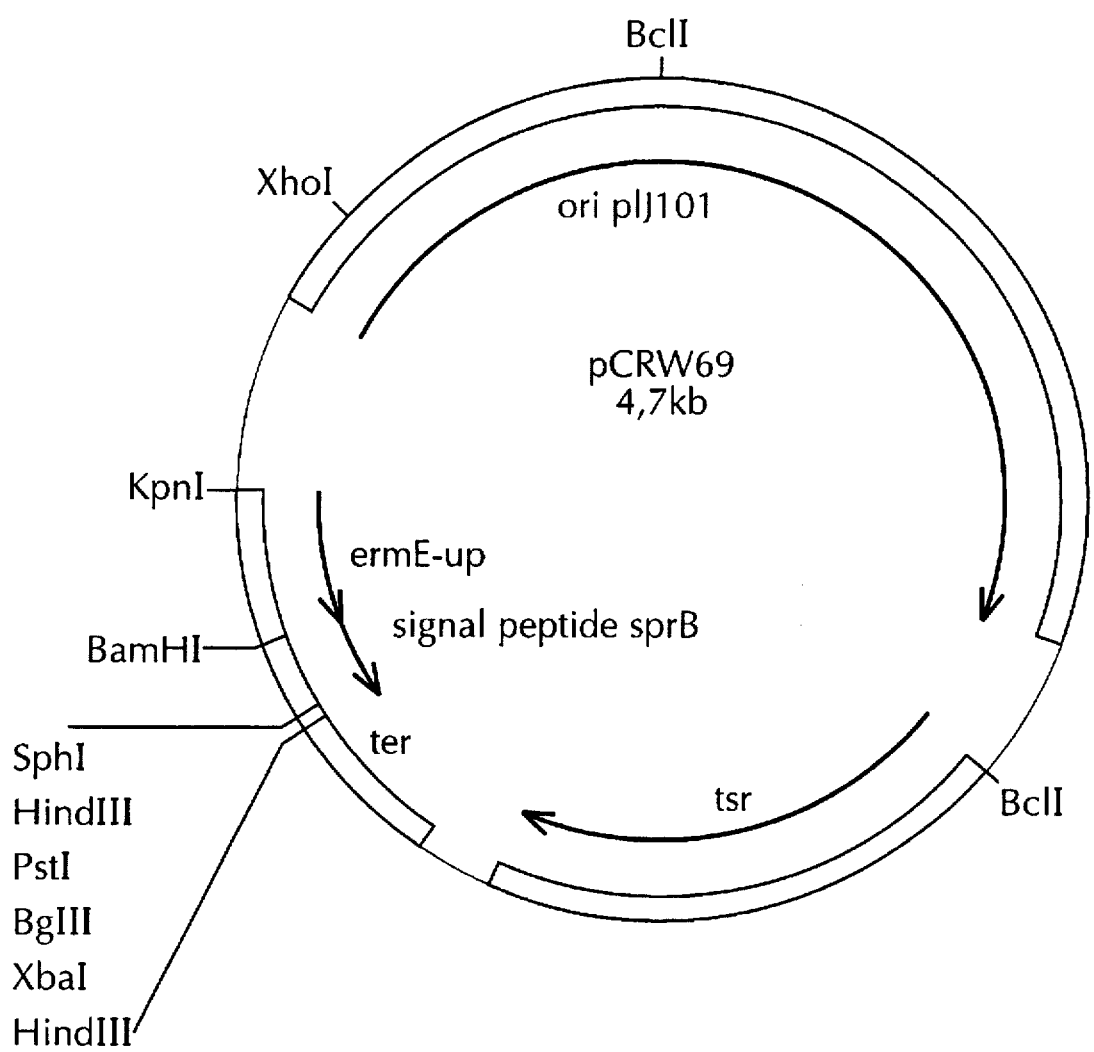
FIG. 1 shows the expression vector pCRW69.
Figure 2:
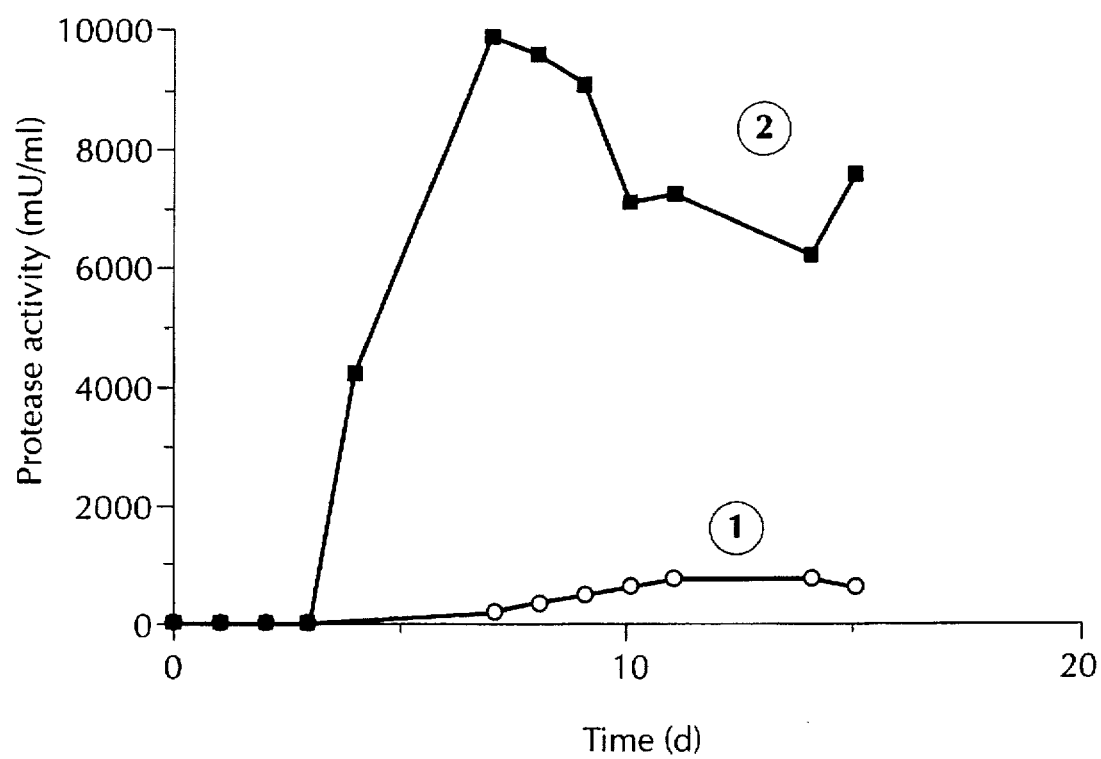
FIG. 2 shows a comparison of the amounts of serine protease B which are obtained after expression in *Streptomyces lividans* 66 TK23 (curve 1), and Streptomyces galbus, DSM 40480 (curve 2).

This BamHI/SmaI fragment is ligated into vector pIJ4070 cleaved with BamHI/HindII that contains the ermE-up promoter (SEQ ID NO: 1) and a multilinker, and the plasmid pCRW68 obtained in this way is transformed in *E. coli* JM83 (Messing et al., Gene 33 (1985), 103–119). The promoter-signal peptide multilinker cassette comprising 420 bp that is formed in this way is inserted as a BglII/KpnI fragment of pCRW68 into the vector pIJ699 cleaved with KpnI and BglII by which means the streptomycetes vector pCRW69 is formed with an extended polylinker (FIG. 1).

EXAMPLE 2

Cloning of the protease B gene from *Streptomyces griseus* DSM 40236.

The DNA section coding for serine protease B of *Streptomyces griseus*, including the ribosome binding site, signal peptide and propeptide (sequence given in: Henderson et al., J. Bacteriol. 169 (1987), 3778–3784) is amplified by PCR from the genomic DNA of *Streptomyces griseus* DSM 40236 using partially non-homologous oligonucleotide primers (SEQ ID NO:4 and SEQ ID NO:5) it is mutated in this process in such a way that this region becomes accessible as a BamHI/PstI fragment. This 1.0 kb long BamHI/PstI fragment is ligated into the vector pCRW69 digested with BamHI/PstI and the vector pCRW70, obtained in this way is transformed in *Streptomyces galbus* (example 6). By digestion of this vector pCRW70 with SphI and with an enzyme that cuts in the multilinker region, pCRW70 enables various genes to be cloned under the control of the ermE-up promoter.

EXAMPLE 3

Cloning of the Gene for Alkaline Phosphatase phoA from *Escherichia coli* 294

The phoA gene is prepared from the DNA of *E. coli* 294 as a HindIII/XhoI fragment as described by Chang et al., (Chang et al., Gene 44 (1986), 121–125) and cloned into a pUC18 vector digested with HindIII/SalI (Messing et al., Gene 33 (1985), 103–119) in *E. coli* JM83. The region coding for mature alkaline phosphatase is amplified as a 1.36 kb long PstI/XbaI fragment by PCR mutagenesis using the primers shown in SEQ ID NO:6 and SEQ ID NO:7 and ligated into vector pCRW69 (example 1) digested with PstI/XbaI.

EXAMPLE 4

Cloning of Human Colipase cDNA

The gene section for mature human colipase from the pancreas (Lowe et al., Biochem 29 (1989), 823–828) is obtained as a PCR fragment from a λgt11 gene bank (Clontech Laboratories, Inc., Palo Alto, Calif., USA, Cat. No. HL 1069b) by amplification during, which a SphI cleavage site is inserted at the 5' end and a PstI cleavage site is inserted at the 3' end by PCR mutagenesis using the primers shown in SEQ ID NO:8 and SEQ ID NO:9. The 340 bp long fragment is ligated into vector pCRW69 (example 1) and digested with SphI/PstI, during which the gene is altered in the region of the fusion site.

EXAMPLE 5

Cloning of Human Pancreatic Amylase cDNA

Human pancreatic amylase cDNA is cloned as follows: The sequence coding for mature amylase (Nakamura et al., Gene 28 (1984), 263–270 and Nishide et al., Gene 50 (1986), 371–372) is amplified by means of PCR from a commercial cDNA gene bank in λgt11 (Clontech Laboratories, Inc., Palo Alto, Calif., USA, Cat. No. HL 1069b) and by using partially non-homologous primers (SEQ ID NO:10 and SEQ ID NO:11). It is altered in such a way that it becomes accessible as a SphI/HindIII fragment. The 1.53 kb long SphI/HindIII fragment is ligated into vector pCRW69 digested with SphI/HindIII.

EXAMPLE 6

Formation of Protoplasts and Transformation of *Streptomyces galbus*, DSM 40480

*Streptomyces galbus*, strain DSM 40480 is transformed in accordance with Chater et al. (Chater et al., Current Topics Microbiol. 46 (1982), 69–95). For the protoplast formation, 25 ml main culture in TSB (tryptone-soyabroth; oxoid 30 g/l) or YEME medium (both containing 10.3% sucrose but without glycine) is inoculated in a 250 ml Erlenmeyer flask with 2 ml of a stationary pre-culture of *Streptomyces galbus* in TSB and it is incubated for 36 hours at 28° C. while shaking intensively. Subsequently the culture is divided into 2 sterile centrifuge tubes, centrifuged for 10 minutes at 2600 g and 4° C. and the mycelium is washed twice with a 10.3% sucrose solution. Afterwards the cells are incubated for 45 minutes at 30° C. in 4 ml P buffer containing lysozyme (1 mg/ml), and the suspension is pipetted up and down three times with a 5 ml glass pipette and incubated for a further 15 minutes. After addition of 5 ml P buffer and mixing with a pipette as above, it is filtered through sterile cotton wool. The protoplasts obtained in this manner are centrifuged (7 minutes, 1500 g), resuspended in 4 ml P buffer in each case and slowly frozen on ice in 1 ml aliquots in 1.5 ml reaction vessels at −70° C.

For the transformation an aliquot of the frozen protoplasts is quickly thawed at 37° C., centrifuged for 4 minutes at room temperature and 3000 g, the pellet is resuspended in the remaining drop and admixed with a maximum of 5 μl DNA solution. After addition of 100 μl 25% (w/v) PEG 1000 (Riedel de Haën) in T buffer and mixing by drawing it up into and withdrawing it three times from the tip of a shortened 200 μl plastic pipette, it is immediately diluted with 850 μl P buffer, centrifuged for 4 minutes as above at room temperature and the pellet is resuspended in 1 ml P buffer.

In order to regenerate the protoplasts after the transformation, they are plated out on R2YE agar plates (predried for 1 hour in a sterile bank) and regenerated for ca. 30 hours at 20°–25° C. After coating with P buffer containing thiostreptone (300 μg/ml), the cultures are selected by incubating further at 30° C.

| TSB/10.3% sucrose | |
|---|---|
| TSB instant medium (Oxoid) | 30.0 g/l |
| sucrose | 103.0 g/l |
| YEME medium/10.3% sucrose | |
| yeast extract | 3.00 g/l |
| peptone | 5.00 g/l |
| malt extract | 3.00 g/l |
| glucose | 10.00 g/l |
| sucrose | 103.00 g/l |
| $MgCl_2 \times 6 H_2O$ | 1.02 g/l |
| P buffer | |
| Sucrose | 103.0 g/l |
| $K_2SO_4$ | 0.20 g/l |
| $MgCl_2 \times 6 H_2O$ | 2.02 g/l |
| trace element solution | 2.0 ml | distilled water 800.0 ml autoclave in 80 ml aliquots and subsequently

| | |
|---|---|
| $KH_2PO_4$ (0.5%) | 1 ml |
| $CaCl_2 \times H_2O$ (3.68%) | 10 ml |
| TES buffer (5.73%, pH 7.2) | 10 ml | are added by pipette under sterile conditions.

TES buffer: 5.73 g TES (N-tris(hydroxymethyl)methyl-2aminoethanesulphonic acid, SERVA) weigh into 95 ml distilled water and adjust the pH to pH 7.2 with 2 mol/l NaOH, subsequently make it up to 100 ml and autoclave.

| Trace element solution | |
|---|---|
| $ZnCl_2$ | 40.0 mg/l |
| $FeCl_3 \times 6 H_2O$ | 200.0 mg/l |
| $CuCl_2 \times 2 H_2O$ | 10.0 mg/l |
| $MnCl_2$ | 10.0 mg/l |
| $Na_2B_4O_7 \times 10 H_2O$ | 10.0 mg/l |
| $(NH_4)_6 Mo_7O_4 \times 4 H_2O$ | 10.0 mg/l |
| T buffer | |
| sucrose (10.3%) | 25.0 ml |
| distilled water | 75.0 ml |
| trace element solution | 0.2 ml |
| $K_2SO_4$ (2.5%) | 1.0 ml | autoclave in aliquots each of 9.3 ml and subsequently add by pipette under sterile conditions: $CaCl_2 \times 6 H_2O$ (3.68%): 0.2 ml, TM buffer pH 8.0:0.5 ml TM buffer Adjust 1 mol/l Tris to pH 8.0 with maleic acid (solid) and autoclave.

T buffer/25% PEG

Weigh 0.5 g PEG 1000 (Riedel de Haën) and autoclave. Liquify again immediately before use and add 1.5 ml T buffer by pipette under sterile conditions.

| R2YE agar | |
|---|---|
| sucrose | 103.0 g/l |
| $MgCl_2$ | 10.12 g/l |
| glucose | 10.0 g/l |
| $K_2SO_4$ | 0.25 g/l |
| casamino acids | 0.1 g/l |
| agar-agar (Bacto-Agar, Difco Company) | 25.0 g/l | make up to 800 ml with distilled water, autoclave and afterwards add

| | |
|---|---|
| $KH_2PO_4$ (0.5%) | 10.0 ml |
| $CaCl_2 \times 2H_2O$ (3.68%) | 80.0 ml |
| L-proline (20.0%) | 15.0 ml |
| TES buffer (5.73%) pH 7.2) | 100.0 ml |
| trace element solution | 2.0 ml |
| NaOH (1 mol/l) | 5.0 ml |
| yeast extract (Difco) (10.0%) | 50.0 ml | under sterile conditions.

EXAMPLE 7

Expression of Recombinant Proteins in *Streptomyces galbus* DSM 40480

*Steptomyces galbus* DSM 40480 is transformed according to example 6 using the gene sequences cloned according to examples 2–5. The transformed bacteria are cultured under the following conditions in order to express the cloned genes:

a) Expression of Protease B from *Streptomyces griseus*

Low-fat milk minimal medium (MM medium) is used for the optimal production of protease B. 100 ml cultures are grown at 30° C. in 1000 ml Erlenmeyer flasks while aerating vigorously (Gyrotory water-bath shaker from the Brunswick Scientific Company, Model G 76; shaking rate: 8). After a period of 2–4 days the formation of protease starts which can be monitored directly by the clearing of the medium.

| MM medium | |
|---|---|
| NaCl | 5.00 g |
| $MgSO_4$ | 0.20 g |
| $FeSO_4$ | 0.01 g |
| $(NH_4)_2 SO_4$ | 2.00 g* |
| $CaCl_2$ | 0.36 g* |
| $K_2HPO_4$ | 0.50 g* |
| glucose | 10.0 g* |
| milk powder | 2.0 g* | which the salts that are not labelled with *, make up to 825 ml with redistilled water, stir for 10 minutes and then adjust the pH value to 7.0 to 7.5 with NaOH. Dissolve the other medium components labelled with * separately in 25 ml in each case, dissolve glucose in 50 ml water distilled three times, autoclave and subsequently add them to the autoclaved salt solution under sterile conditions.

b) Expression of Alkaline Phosphatase from *E. coli*

The alkaline phosphatase from *E. coli* is produced in TSB medium under the culture conditions described in section a) for protease B.

c) Expression of Human Pancreatic Amylase

In order to produce human pancreatic amylase the respectively transformed *Streptomyces galbus* is cultured in 100 ml Lechevalier medium containing 1% starch under the conditions stated in section a).

| Lechevalier/1% starch | |
|---|---|
| starch | 10.00 g/l |
| L-asparagine | 10.00 g/l |
| $ZnSO_4 \times 7 H_2O$ | 0.02 g/l |
| $MgSO_4 \times 7 H_2O$ | 0.20 g/l |
| $FeSO_4 \times 7 H_2O$ | 0.02 g/l |
| $CuSO_4 \times 5 H_2O$ | 0.02 g/l |
| $K_2HPO_4$ | 0.88 g/l |
| $KH_2PO_4$ | 0.68 g/l | pH value 7.2 d) Expression of Human Colipase

The expression of human colipase is carried out as described under a), but in TSB medium/10.3% sucrose or YEME medium/10.3% sucrose (without glycine in each case).

EXAMPLE 8

Comparison of the expression of serine protease B in *Streptomyces lividans* 66 TK23 and *Streptomyces galbus* DSM 40480.

The 2.8 kb long BglII fragment of the sprB gene coding for the serine protease B of *Streptomyces griseus* (sequence shown in: Henderson et al., J. Bacteriol. 169 (1987), 3778–3784) is cloned into the pUC18 vector cleaved with BamHI by which means the vector pAWD7-14 is obtained. A 2.7 kb long PstI/KpnI fragment that contains the complete sprB gene including the sprB promoter is isolated from this vector and ligated into the vector pIJ702 (Katz et al., J. Gen. Microbiol. 129 (1983), 2703–2714) which was also cleaved with PstI/KpnI. *Streptomyces galbus* DSM 40480 and *Streptomyces lividans* 66 TK23 (Hopwood et al., (1985) in Genetic Manipulation of *Streptomyces*, A laboratory manual, The John Innes Foundation: Norwich) were transformed according to the method described in example 6 using the vector pAWS7-14-4 obtained in this way.

The protease expression of the transformed cells was determined according to the method of Delmar et al. (Anal. Biochem. 99 (1979), 316–320 and Geiger (Methods enzymatic assay) Bergmeyer editor (1984), 815–818). 70 µl substrate solution (N-succinyl-Ala-Ala-Pro-Phe-p-nitroanilide, 3,12 mg/ml in 50 mmol/l sodium-potassium phosphate buffer pH 8), and 620 µl 50 mmol/l sodium-potassium phosphate buffer pH 8 (50 mmol/l $Na_2HPO_4$, and 50 mmol/l $KH_2PO_4$) are placed in a microcuvette, mixed and preincubated for 5 minutes at 30° C. in a cuvette that can be heated. The reaction is started by the addition of 10 µl culture supernatant of the bacterial strains to be examined and immediately afterwards the increase in the absorbance is measured at 405 nm for at least 5 minutes. The volume activity is given by $$\text{Volume activity} = \frac{A\ 405\ \text{nm/min} \times \text{dilution} \times V_{total}}{\epsilon\ 405\ \text{nm} \times d \times V\ \text{sample}}$$

$V_{total}$: total volume (0.7 ml)

V sample: sample volume (0.01 ml)

d : light path of the cuvette (1 cm)

$\epsilon$405 nm : molar absorption coefficient (9.304 $M^{-1}\ cm^{-1}$)

---

We claim:

1. A method of producing a recombinant protein comprising:

(a) transforming *Streptomyces galbus* DSM 40480 strain cells with an expression vector containing DNA which codes for said protein under conditions which allow for the expression of said protein from said cells; and (b) expressing said protein.

2. The method of claim 1 wherein the expression vector comprises SEQ ID NO:1.

3. The method of claim 1, wherein the DNA in the expression vector is under the control of a promoter selected from the group consisting of an erm E promoter, and an erm-up promoter.

4. The method of claim 1 wherein the DNA in the expression vector is under the control of an inducible promoter.

5. The method of claim 4 wherein the inducible promoter is a Gal P1 promoter from the galactose operon of *Streptomycetes lividans*.

* * * * *

UNITED STATES PATENT AND TRADEMARK OFFICE
CERTIFICATE OF CORRECTION

PATENT NO. : 5,656,453
DATED : August 12, 1997
INVENTOR(S) : Piepersberg et al.

It is certified that error appears in the above-indentified patent and that said Letters Patent is hereby corrected as shown below:

In column 1, line 28, change "Weib" to -- Weiss --.

In column 2, line 29, change "*E. Coli*" to -- *E. coli* --.

In column 2, line 41, change "Streptomyces galbus" to -- *Streptomyces galbus* --.

In column 3, line 32, delete "it" and insert therefor -- . It --.

In column 3, lines 32-33, delete "in this process".

In column 3, line 35, after "pCRW69" insert -- , --.

In column 5, line 28, after "2" insert -- - --

In column 6, line 40, change "which" to -- Weigh --; also change "*, make" to -- *. Make --.

Signed and Sealed this

Sixteenth Day of November, 1999

Attest:

*Attesting Officer*

Q. TODD DICKINSON

*Acting Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: genomic ( x i ) SEQUENCE DESCRIPTION: SEQ ID NO: 1:

```
AGATCTGGGG  AATTCGAGCT  CGGTACCAGC  CCGACCCGAG  CACGCGCCGG  CACGCCTGGT   60

CGATGTCGGA  CCGGAGTTCG  AGGTACGCGG  CTTGCAGGTC  CAGGAAGGGG  ACGTCCATGC  120

GAGTGTCCGT  TCGAGTGGCG  GCTTGCGCCC  GATGCTAGTC  GCGGTTGATC  GGCGATCGCA  180

GGTGCACGCG  GTCGATCTTG  ACGGCTGGCG  AGAGGTGCGG  GGAGGATCTG  ACCGACGCGG  240

TCCACACGTG  GCACCGCGAT  GCTGTTGTGG  GCACAATCGT  GCCGGTTGGT  AGGATCCTCT  300

AGAGTCGACC  GGCATGCAAG  CTTGGCTGCA  GATCT                                335
```

( 2 ) INFORMATION FOR SEQ ID NO: 2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

```
     GGATCCCCCT CGGAGGAACC CGAA                                                     24
```

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
     CGTCCCGGGC GTTTCGGCTC GC                                                       22
```

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
     GGATCCCCCT CGGAGGAACC CGGCATGCGG                                               30
```

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
     CTGCAGAGCT CCCCGGCGAG CGGGAGCC                                                 28
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
     TTCTGCAGTT CTGGAAAACC GGGC                                                     24
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
     AATCTAGATT ATTTCAGCCC CAGA                                                     24
```

(2) INFORMATION FOR SEQ ID NO: 8:

```
      ( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO: 8:

ATTGCATGCA TATGCAGCTC CTGG                                              24

( 2 ) INFORMATION FOR SEQ ID NO: 9:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO: 9:

CTGCAGCATT CTGGGCTAGG TGTG                                              24

( 2 ) INFORMATION FOR SEQ ID NO: 10:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO: 10:

TTCGGCATGC TTGCTGGGCT CAGT                                              24

( 2 ) INFORMATION FOR SEQ ID NO: 11:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO: 11:

AAGCTTTGCG GATTTGCATT TAAT                                              24
```